(12) United States Patent
Nair et al.

(10) Patent No.: US 6,194,469 B1
(45) Date of Patent: Feb. 27, 2001

(54) METHOD FOR INHIBITING CYCLOOXYGENASE AND INFLAMMATION USING CHERRY BIOFLAVONOIDS

(75) Inventors: Muraleedharan G. Nair, Okemos, MI (US); Haibo Wang, Madera, CA (US); Gale M. Strasburg, East Lansing, MI (US); Alden M. Booren, Lansing, MI (US); James I. Gray, Haslett, MI (US)

(73) Assignee: Board of Trustees operating Michigan State Univeristy, East Lansing, MI (US)

( * ) Notice: Subject to any disclaimer, the term of this patent is extended or adjusted under 35 U.S.C. 154(b) by 0 days.

(21) Appl. No.: 09/337,313

(22) Filed: Jun. 21, 1999

Related U.S. Application Data

(63) Continuation-in-part of application No. 09/317,310, filed on May 24, 1999.
(60) Provisional application No. 60/120,178, filed on Feb. 16, 1999, and provisional application No. 60/111,945, filed on Dec. 11, 1998.

(51) Int. Cl.[7] .......................... A61K 7/02; A61K 35/78; A61K 35/02; A62D 3/00; C07D 311/62

(52) U.S. Cl. .................. 514/886; 514/887; 424/195.1

(58) Field of Search .......................... 514/886, 887, 514/439, 195.1, 783; 424/195.1

(56) References Cited

U.S. PATENT DOCUMENTS

| | | |
|---|---|---|
| 4,297,220 | 10/1981 | Meitzner . |
| 4,439,458 | 3/1984 | Puri . |
| 5,266,685 | 11/1993 | Garbutt . |
| 5,665,783 | 9/1997 | Katzakian et al. . |
| 5,817,354 | 10/1998 | Mozaffar . |

FOREIGN PATENT DOCUMENTS 1 589 294   5/1981 (GB) .

OTHER PUBLICATIONS

State News (MSU newspaper) Feb. 3, 1999.
Web download articles—Natural Painkillers and Strong Antioxidants Found in Tart Cherries (Jan. 28, 1999; Tart Cherries May be Natural Pain Reliever (Jan. 29, 1999).
Welton, A.R., et al., Prog. Clin. Biol. Res. 213 231–242 (1986).
Kalkbrenner, F., et al., Pharmacology 44 1–12 (1992).
Wurm, G., et al., Deutche Apotheker Zeitung 122 2062–2068 (1982) (English translation of abstract attached).
Hoppe, H.: Drogenkunde 8. Aufl.p.878, Walter de Gruyter, Berlin—New York (1975)—(Reference 1 of Blazso) (and translation).
Kralik, L.: DE No. 1.117.822 (C 1304) (1961) (and English translation) (Reference 2 of Blazso).
Gellert, M.; et al., in: Farkas, L., et al (eds): Flavonoids and Bioflavonoids (1985) Studies in Organic Chemistry, 23 p. 279, Elsevier, Amsterdam–Oxford–New York–Tokyo (1986) (Reference 3 of Blazso).
Wagner, H., et al., Tetrahedron Lett 19 1471 (1969) (Reference 4 of Blazso) (including English Translation).
Kinsella, et al., Food Tech. 85–89 (1993).
Tsuda, T., et al., J. Agric. Food Chem. 42: 2407–2410 (1994).
Li, K. C., et al., J. Am. Chem. Soc. 78:979–980 (1956).
Harborne, J.B., et al., Phytochemistry 3:453–463 (1964).

(List continued on next page.)

Primary Examiner—Jon P. Weber
Assistant Examiner—Patricia Patten
(74) Attorney, Agent, or Firm—Ian C. McLeod

(57) ABSTRACT

A method for inhibiting cyclooxygenase enzymes and inflammation in a mammal using a cherry or cherry anthocyanins, bioflavonoids and phenolics is described. In particular a mixture including the anthocyanins, the bioflavonoids and the phenolics is described for this use.

8 Claims, 8 Drawing Sheets-

OTHER PUBLICATIONS

Dekazos, E.D., J. Food Sci. 35:237–241 (1970).
Chandra, A., et al., J. Agric. Food Chem. 40:967–969 (1992).
Shrikhande, A.J. and F.J. Francis, J. Food Sci. 38:649–651 (1973).
Chandra, A., et al., J. Agric. Food Chem. 41: 1062–1065 (1993).
Bayer, T., et al., Phytochemistry 28:2373–2378 (1989).
Goda, Y., et al., Chem. Pharm. Bull. 40:2452–2457 (1992).
Humes, J. L., et al., Proc. Natl. Acad. Sci. U.S.A. 78:2053–2056 (1981).
Rome, L. H., et al., Proc. Natl. Acad. Sci. U.S.A. 72:4863–4865 (1975).
Hemler, M., et al., J. Biol. Chem. 25:251–5575–5579 (1976).
Masferrer, J. L., et al., Proc. Natl. Acad. Sci. U.S.A. 91 3228–3232 (1994).
Sanchez De Medina, L. H., et al., J. Pharmacol. Exp. Ther. 278 771–779 (1996).
Baumann, J., et al., Prostaglandins 20 627–640 (1980).
Kimura, Y., et al., Chem. Pharm. Bull. 34 1223–1227 (1986).
Mower, R. L., et al., Biochem. Pharmacol. 33 357–364 (1984).
Wang, H., et al., J. Agric. Food Chem. 45: 2556–2560 (1997).
Arora, A. and G.M. Strasburg, J. Amer. Oil Chem. Soc. 74:1031–1040 (1997).
Meade, E.A., et al., J. Biol. Chem. 268:6610–6614 (1993).
Dewitt, D.L., et al., J. Biol. Chem. 265 5192–5198 (1990).
Moroney, M.A., et al., J. Pharm. Pharmacol. 40 787–792 (1988).
Wang et al., J. Nat. Products 62:294–296 (1999).
Wang et al., J. of Ag. and Food Chemistry, 47:840–844 (1999).
Wang et al., J. of Nat. Products 62:86–88 (1999).
Hoult,J.R.S., et al., Agents Actions 42:44–49 (1994).
Wurm, G., et al., Deutsche Apotheker Zeitung 122.Jahrg. Nr. 41 14.10.1982 (English Translation).
Database Dissertation Abstracts Online! Dialog File 35:1998 Wang, Haibo: "Antioxidant and Anti–Inflammatory Compounds in Tart Cherries (Anthocyanins, Phenolics, Flavonoids, Balaton, Montmorency)" retired from Dialog Database accession No. 01695255 XP002137469 abstract & Dissertation, Michigan State University, East Lansing, MI,USA (1998) Avail UMI; Order No. AAD99–22386 (157 pages).

Kim Kee Hee et al, Antiinflammatory activity of flavonoids:Mouse ear edema inhibition Archives of Pharmacal Research (Seoul), vol. 16, No. 1, pp. 18–24 (1993) XP000886582—tables I–V;concluding paragraph of the discussion.

Blaszo G et al: "Anti–inflammatory effects of cherry (*Prunus avium* L.) stalk extract" Pharmazie, vol. 49, No. 7, pp. 540–541 (1994) XP000887283; p. 540.

Database Caplus Online! Chemical Abstracts Service, Columbus, Ohio, US Selenina, L.V. et al: "polyphenols of *Potentilla erecta* and their biological activity"—retrieved from STN Database accession No. 80:22614 XP002137470 abstract & Rast. Resur. 9(3), 409–414 (1973).

Database Caplus Online!—Chemical Abstracts Services, Columbus, Ohio, US Razga, Zsolt et al: "Effect of benzo–pyranone derivatives on dithranol–induced ear edema in mice" retrieved from STN Database accession No. 110:127910 XP002137471 abstract & Kiserl. Orvostud. (6) 464–471 (1988).

Lee Song Jin et al: "Antiinflammatory activity of isoflavonoids from Peuraria Radix and Biochanin A derivatives" Archives of Pharmacal Research (Seoul), vol. 17, No. 1, pp. 31–35 (1994) XP000886583—tables II, III.

Hernandez–Perez M. et al: "Phenolic composition of the mocan (*Visnea mocanera*)" J. Agric. Food Chem. vol. 44, No. 11, pp. 3512–3515 (1996) XP000632164—abstract.

Sigma–Aldrich–Amberlite XAD–2, 500G specifications.

Borissova et al. Antiinflammatory Effect of Flavonoids in the Natural Juice from *Aronia melanocarpa*, Rutin and Rutin–Magnesium Complex on an Experimental Model of Inflammation Induced by Histamine and Serotonin: Pharmacologica, 20, (1), 25–30, 1994.*

LaBell, F. Antioxidants Isolated from Tart Cherries: Prepared Foods, pp. 97–98, Jun. 1998.*

Blazso et al. Anti–Inflammatory Effect of Cherry (*Prunus avium* L.) Stalk Extract: Pharmazie, 49, H. 7, pp. 540–541, 1994.*

* cited by examiner

Anthocyanin 1
(cyanidin-3-
glucosylrutinoside)

Anthocyanin 2
(cyanidin-3-
rutinoside)

H

Anthocyanin 3
(cyanidin-3-glucoside)

H

H

| Compound | $R_2$ | $R_3$ | $R_5$ | $R_6$ | $R_7$ |
|---|---|---|---|---|---|
| Quercetin | OH | OH | H | OH | H |
| Kaempferol | H | OH | H | OH | H |
| Luteolin | OH | H | H | OH | H |
| Quercitrin | OH | rhamnose | H | OH | H |
| Kaempferol 3-rutinoside | H | rutinose | H | OH | H |
| 3'-methoxy kaempferol 3-rutinoside | OMe | rutinose | H | OH | H |
| 5,8,4'-trihydroxyl-6,7-dimethoxyflavone | H | H | OMe | OMe | OH |

| Compound | $R_1$ | $R_2$ | $R_3$ |
|---|---|---|---|
| Genistein | OH | OH | OH |
| Genistin | OH | OH | glucose |
| Biochanin A | OMe | OH | OH |
| Daidzein | OH | H | OH |
| Formononetin | OMe | H | OH |

METHOD FOR INHIBITING CYCLOOXYGENASE AND INFLAMMATION USING CHERRY BIOFLAVONOIDS

CROSS REFERENCE TO RELATED APPLICATIONS

This application is a continuation-in-part of U.S. Ser. No. 09/317,310, filed May 24, 1999. This application is based upon Provisional application Ser. No. 60/111,945, filed Dec. 11, 1998. This application is also based upon U.S. Provisional Application Ser. No. 60/120,178, filed Feb. 16, 1999.

STATEMENT REGARDING FEDERALLY SPONSORED RESEARCH OR DEVELOPMENT

None

BACKGROUND OF THE INVENTION

1. Summary of the Invention

The present invention relates to a method of use of at least one compound isolated from cherries as cyclooxygenase (COX-1 and COX-2) inhibitors. In particular, the present invention provides a natural cherry composition containing a mixture of anthocyanins, bioflavonoids and phenolics for use as anti-inflammatory agents as a result of inhibition of the cyclooxygenase enzymes.

2. Description of Related Art

Many plant-derived compounds may also impart important positive pharmacological or "nutraceutical/ phytoceutical" traits to foods by way of their abilities to serve as antioxidants by maintaining low levels of reactive oxygen intermediates, as anti-inflammatory agents by inhibiting prostaglandin synthesis, or as inhibitors of enzymes involved in cell proliferation. These activities may be important in ameliorating chronic diseases including cancer, arthritis, and cardiovascular disease (Kinsella et al., Food Tech. 85–89 (1993). Thus, with natural products, the dietary supplement/food industry and neutraceutical/phytoceutical companies have the opportunity to employ compounds which can not only enhance food stability as effectively as synthetic antioxidants, but can also offer significant health benefits to the consumer.

Cherries are thought to have beneficial health properties in general. Consumption of cherries was reported to alleviate arthritic pain and gout (Hamel, P. B., et al. Cherokee Plants 28: Herald: Raleigh, N. C. (1975)) although there is no evidence for its active components or mode of action. These beneficial effects may be partially associated with the abundance of anthocyanins, the glycosides of cyanidin.

*Prunus Cerasus* L. (Rosacease), cv. MONTMORENCY is the major tart cherry commercially grown in the United States. In order to challenge the MONTMORENCY monoculture, a new cultivar, BALATON tart cherry (*Ujferbertoi furtos*), was introduced into the United States in 1984, and has been tested in Michigan, Utah, and Wisconsin. BALATON produces fruits darker than MONTMORENCY.

Colorants like anthocyanins have been regarded as the index of quality in tart cherries. Most importantly, recent results showed that anthocyanins such as cyanidin-3-glucoside have strong antioxidant activities (Tsuda, T., et al, J. Agric. Food Chem. 42:2407–2410 (1994)).

Early studies have showed that MONTMORENCY cherry contains the anthocyanins cyanidin-3-gentiobioside and cyanidin-3-rutinoside (Li, K. C., et al., J. Am. Chem. Soc. 78:979–980 (1956)). Cyanidin-3-glucosylrutinoside was also found in six out of the seven sour cherry varieties (Harborne, J. B., et al., Phytochemistry 3:453–463 (1964)). Dekazos (Dekazos, E. D., J. Food Sci. 35:237–241 (1970)) reported anthocyanin pigments in MONTMORENCY cherry as peonidin-3-rutinoside peonidin and cyanidin along with cyanidin-3-sophoroside, cyanidin-3-rutinoside and cyanidin-3-glucoside. However, cyanidin-3-glucosylrutinoside as well as cyanidin-3-glucoside, cyanidin-3-sophoroside and cyanidin-3-rutinoside were identified as main pigments in sour cherries. Using HPLC retention values, Chandra et al (Chandra, A., et al., J. Agric. Food Chem. 40:967–969 (1992)) reported that cyanidin-3-sophoroside and cyanidin-3-glucoside were the major and minor anthocyanins, respectively, in Michigan grown MONTMORENCY cherry. Similarly, cyanidin-3-xylosylrutinoside was detected as a minor pigment in MONTMORENCY cherry (Shrikhande, A. J. and F. J. Francis, J. Food Sci. 38:649–651 (1973)).

In the prior art, production of pure anthocyanins (compounds 1–3 of FIG. 1) from BALATON and MONTMORENCY cherry juices was carried out first by adsorbing the pigment on an AMBERLITE XAD-2 (Sigma Chemicals) column (Chandra, A., et al., J. Agric. Food Chem. 41:1062–1065 (1993)). The column was washed with water until the eluant gave a pH of approximately 7.0. The adsorbed pigments along with other phenolics were eluted with MeOH. The resulting crude anthocyanins were fractionated and purified by C-18 MPLC and HPLC, respectively, to afford pure anthocyanins for spectral studies. Purification of 500 mg crude MONTMORENCY anthocyanins from AMBERLITE XAD-2 yielded 60 mg of pure anthocyanins 1–3 compared to 391.43 mg from BALATON. This research indicated that crude anthocyanins from MONTMORENCY obtained from the XAD-2 contained a high percentage of other organic compounds. There was no attempt to use the crude mixture of phenolics and anthocyanins for any purpose. U.S. Pat. Nos., 5,266,685 to Garbutt, 5,665,783 to Katzakian et al and 5,817,354 to Mozaffar describe various adsorbent resins and their use for isolating unrelated products. These patents are only illustrative of the general state of the art in the use of adsorbent resins.

Cyclooxygenase (COX) or prostaglandin endoperoxide H synthase (PGHS-1, PGHS-2 or COX-1/COX-2) enzymes are widely used to measure the anti-inflammatory effects of plant products (Bayer, T., et al., Phytochemistry 28 2373–2378 (1989); and Goda, Y., et al., Chem. Pharm. Bull. 40 2452–2457 (1992)). COX enzyme is the pharmacological target site for the nonsteroidal anti-inflammatory drug discovery (Humes, J. L., et al., Proc. Natl. Acad. Sci. U.S.A. 78 2053–2056 (1981); and Rome, L. H., et al., Proc. Natl. Acad. Sci. U.S.A. 72 4863–4865 (1975)). Two isozymes of cyclooxygenase involved in prostaglandin synthesis are cyclooxygenase-1 (COX-1) and cyclooxygenase-2 (COX-2), respectively (Hemler, M., et al., J. Biol. Chem. 25 251, 5575–5579 (1976)). It is hypothesized that selective COX-2 inhibitors are mainly responsible for anti-inflammatory activity (Masferrer, J. L., et al., Proc. Natl. Acad. Sci. U.S.A. 91 3228–3232 (1994)). Flavonoids are now being investigated as anti-inflammatory substances as well as their structural features for cyclooxygenase (COX) activity. The 5,7-dihydroxyflavone, galangin with an $IC_{50}$ of 5.5 $\mu M$, was found to be the most active cyclooxygenase inhibitory flavonoid (Wurm, G., et al., Deutche Apotheker Zeitung 122 2062–2068 (1982)). Flavonoids with an ortho-dihydroxy in ring A or B were stronger inhibitors than those with a free 3-OH group (Wurm, G., et al., Deutche Apotheker Zeitung 122 2062–2068 (1982); and Baumann, J., et al., Prostaglandins 20 627–640 (1980)). The $C_2$–$C_3$ double bond, which determines the coplanarity of the hetero rings appears to be a major determinant of COX activity (Wurm, G., et al., Deutche Apotheker Zeitung 122 2062–2068 (1982)). Certain prenylated flavonoids, such as morusin, were also active, because of their higher lipophilicity (Kimura, Y., et al., Chem. Pharm. Bull. 34 1223–1227 (1986)). Also, unsubstituted flavone is a good COX inhibitor (Mower, R. L., et al., Biochem. Pharmacol. 33 357–364 (1984); and Welton, A. F., et al., Prog. Clin. Biol. Res. 213 231–242 (1986)). Most of the flavanones studied in the past did not show significant COX inhibition, except for the flavanone-3-ol, silibinin (Kalkbrenner, F., et al., Pharmacology 44 1–12 (1992)). However, the structure-activity relationships of isoflavonoids are not reported.

There is a need for natural product derived compositions for use as cyclooxygenase inhibitors and as antiinflammatory agents.

SUMMARY OF THE INVENTION

The present invention relates to a method for inhibiting cyclooxygenase or prostaglandin H synthase enzymes which comprises: providing at least one compound isolatable from a cherry with at least one of the enzymes to inhibit the enzymes.

Further, the present invention relates to a method for inhibiting cyclooxygenase or prostaglandin H synthase enzymes which comprises: providing at least one bioflavonoid compound isolatable from a cherry with at least one of the enzymes to inhibit the enzymes.

Further, the present invention relates to a method for inhibiting inflammation in a mammal which comprises: administering at least one compound isolatable from a cherry to the mammal to inhibit inflammation.

Further, the present invention relates to a method for inhibiting inflammation in a mammal which comprises: administering at least one bioflavonoid, anthocyanin or phenolic compound isolated from a cherry to the mammal to inhibit the inflammation.

Finally, the present invention relates to a method for inhibiting inflammation in a mammal which comprises administering cyanidin to the mammal to inhibit inflammation.

The term "anthocyanins" includes the color producing compounds contained in cherries. For the purpose of this application this incudes the aglycone cyanidin.

The term "bioflavonoids" means the isoflavonoid and flavonoid compounds contained in cherries.

The term "phenolics" refers to compounds with a phenyl group and having one or more hydroxyl groups.

The compounds isolated from cherries are most useful with living material. The living material can be in an animal or human. It can also be in tissue culture.

OBJECTS

It is therefore an object of the present invention to provide a cherry compound which can be used as cyclooxygenase inhibitors and anti-inflammatory agents. Further, it is an object of the present invention to provide a method for isolating the composition on a commercial scale. Finally, it is an object of the present invention to provide a natural source compound which is economical to prepare and easy to use. These and other objects will become increasingly apparent by reference to the following description and the drawings.

DESCRIPTION OF PREFERRED EMBODIMENTS

Figure 1:
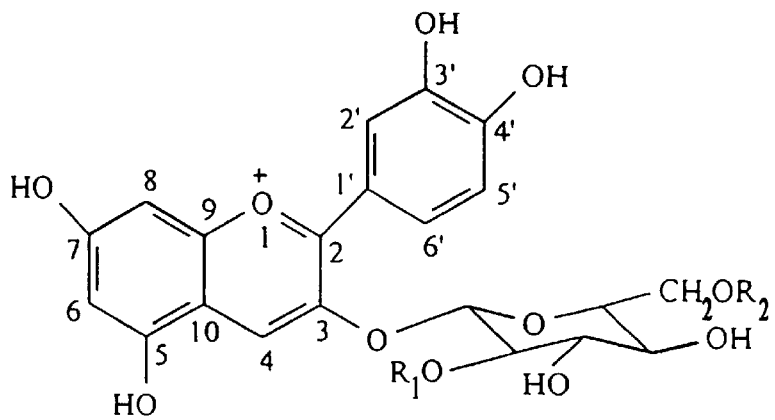
FIG. 1 shows the structure of the isolated anthocyanins (colorants) from BALATON and MONTMORENCY cherries. The aglycon cyanidin has a hydroxyl group at position 3.
Figure 1:
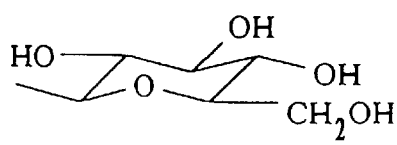
Figure 1:
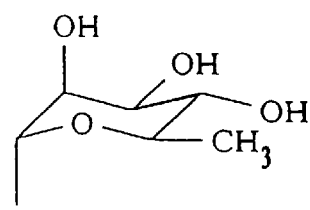
Figure 1:
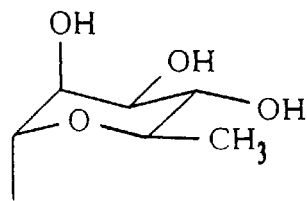

The isolates are preferably prepared as a mixture of anthocyanins, bioflavonoids and phenolics by a method for producing a mixture comprising anthocyanins, bioflavonoids and phenolics from cherries as a composition which comprises:

(a) providing an aqueous solution containing the anthocyanins, bioflavonoids and phenolics from the cherries;

(b) removing the anthocyanins, bioflavonoids and phenolics onto a resin surface from the aqueous solution;

(c) eluting the resin surface with an eluant to remove the anthocyanins, bioflavonoids and phenolics from the resin surface; and (d) separating the eluant from the anthocyanins, bioflavonoids and phenolics.

The cherries used to produce the isolates can be sweet or sour. Tart cherries contain high levels of malic acid in addition to other organic acids which contributes to the sour taste of tart cherries. The method isolates malic acid and other organic acids containing sugars which can be used in foods to provide tartness and flavor. Most preferred are the BALATON and MONTMORENCY cherries.

The isolated mixture of anthocyanins, bioflavonoids and phenolics can be tableted and used as a natural nutraceutical, phytoceutical or dietary supplement. In general, the tablets provide a daily dose of the anthocyanins and bioflavonoids of about 1 to 200 mg, preferably a daily dose of 10–100 mg. One hundred (100) cherries provide 10 to 100 mg of anthocyanins and bioflavonoids. The phenolics (FIG. 4) are provided in an amount of 0.1 to 100 mg as a daily dose. One hundred cherries provide 1–50 mg of phenolics. The amount of the anthocyanins, bioflavonoids and phenolics can be adjusted by isolating the individual compounds and blending them together. It is preferred to use the natural mixture of the anthocyanins, bioflavonoids and phenolics which is isolated by the method using the adsorbent resin.

The resin has a surface to which the anthocyanins, bioflavonoids and the phenolics are adsorbed. A preferred class of adsorptive resins are polymeric crosslinked resins composed of styrene and divinylbenzene such as, for example, the AMBERLITE series of resins, e.g., AMBERLITE XAD-4 and AMBERLITE XAD-16, which are available commercially from Rohm & Haas Co., Philadelphia, Pa. Other polymeric crosslinked styrene and divinylbenzene adsorptive resins suitable for use according to the invention are XFS-4257, XFS-4022, XUS-40323 and XUS-40322 manufactured by The Dow Chemical Company, Midland, Mich., and the like.

It is preferred to use commercially available, FDA-approved, styrene-divinyl-benzene (SDVB) cross-linked copolymer resin, (e.g., AMBERLITE XAD-16). Thus, in the preferred embodiment, AMBERLITE XAD-16, commercially available from Rohm and Haas Company, and described in U.S. Pat. No. 4,297,220, herein incorporated by reference, is used as the resin. This resin is a non-ionic hydrophobic, cross-linked polystyrene divinyl benzene adsorbent resin. AMBERLITE XAD-16 has a macroreticular structure, with both a continuous polymer phase and a continuous pore phase. In a particularly preferred embodiment, the resin used in the present invention has a particle size ranging from 100–200 microns.

It is contemplated that other adsorbents such as those in the AMBERLITE XAD adsorbent series which contain hydrophobic macroreticular resin beads, with particle sizes in the range of 100–200 microns, will also be effective in the methods of the present invention. Moreover, different variations of the AMBERLITES, such as the AMERCHROM CG series of adsorbents, used with particle sizes in the range of 100–200 microns, may also be suitable for use in the present invention. The AMBERLITE XAD-16 is preferred since it can be re-used many times (over 100 times). However, it is contemplated that for food, the use of governmentally-approved resins in the present invention will be considered important and/or desirable.

Any solvent can be used to remove the adsorbed anthocyanins, bioflavonoids and phenolics. Preferred are lower alkanols containing 1 to 4 carbon atoms and most preferred is ethanol (ethyl alcohol) since it is approved for food use. Typically the ethanol is azeotroped with water; however, absolute ethanol can be used. Water containing malic acid and sugars in the cherries pass through the column. These are collected and can be used in foods as flavors.

The anthocyanins, bioflavonoids and phenolics are preferably isolated from the BALATON and the MONTMORENCY cherries. The composition of the cherries is in part shown in part by U.S. application Ser. No. 08/799,788 filed Feb. 12, 1997 and in part U.S. application Ser. No. 60/111,945, filed Dec. 11, 1998 and 60/120,178, filed Feb. 16, 1999, which are incorporated by reference herein.

The term "carrier" or "bulking agent" is used to mean a composition which is added to increase the volume of the composition of the purified composition from the cherry. Preferred is dried cherry pulp. These include any edible starch containing material, protein, such as non-fat dry milk. Within this group are flour, sugar, soybean meal, maltodextrin and various condiments, such as salt, pepper, spices and herbs, for instance. The bulking agent is used in an amount between about $10^{-6}$ and $10^6$ parts by weight of the mixture.

The ratio of anthocyanins, bioflavonoids and phenolics to the carrier is between 0.1 to 100 and 100 to 0.1.

The composition is introduced into the food in an amount between about 0.1 and 10 mg/gm of the active ingredients of the food. The amount is preferably selected so as to not affect the taste of the food and to produce the most beneficial result. The food can be high (wet) or low moisture (dry) as is well known to those skilled in the art. When used as a dietary supplement the tablets contain between 0.1 to 1 gram of active ingredient.

Figure 2:
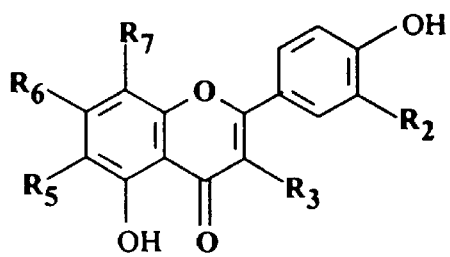
FIGS. 2 and 3 are drawings showing the major bioflavonoids isolated from the cherries.
Figure 3:
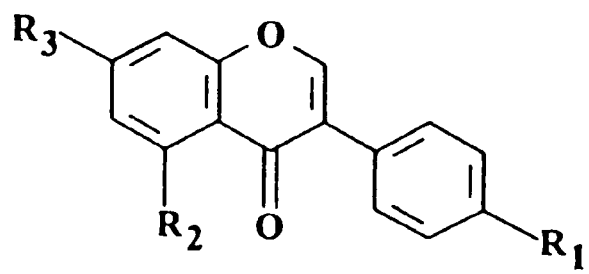

Methods have been developed for extraction and isolation of phytochemicals (Chandra, A., et al., J. Agric. Food Chem. 41:1062 (1992); Wang, H., et al., J. Agric. Food Chem. 45:2556–2560 (1997)) and for rapid screening of antioxidant activity (Arora, A. and G. M. Strasburg, J. Amer. Oil Chem. Soc. 74:1031–1040 (1997)). These methods are being utilized to identify, characterize and test the compounds from BALATON and MONTMORENCY cherries. Juiced cherry tissue was sequentially extracted with hexane, ethyl acetate and methanol. Both methanol and ethyl acetate fractions showed strong antioxidant activity in the screening assay. The ethyl acetate fraction was further purified by silica gel vacuum liquid chromatography to yield four subfractions; the subfraction was further separated into seven fractions by preparative reverse phase HPLC. FIGS. 2 and 3 show the bioflavonoids isolated from the BALATON cherries. There are thus numerous analogous or homologous compounds in the tart cherries. The anthocyanin components obtained from the juice fraction also have been identified and fully characterized (Chandra, A., et al., J. Agric. Food Chem. 41:1062 (1992); Wang, H., et al., J. Agric. Food Chem. 45:2556–2560 (1997)).

Figure 4:
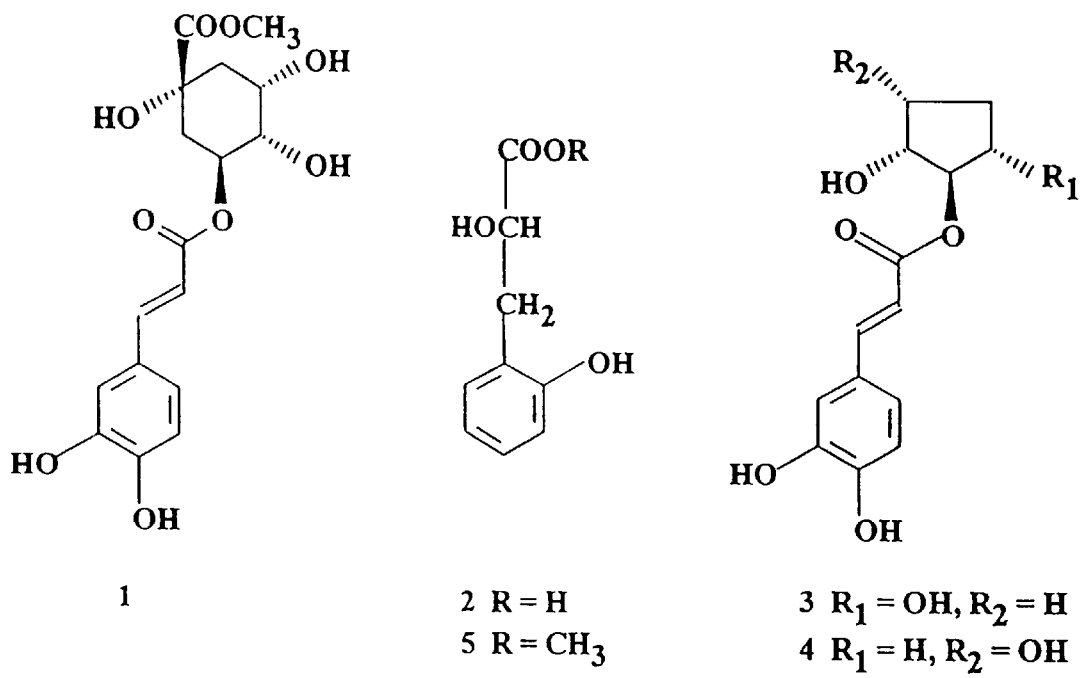
FIG. 4 shows the phenolics isolated from tart cherries.

Two novel phenolic compounds were identified:
I) 1-(3'-4'-dihydroxy cinnamoyl)-2,3-dihydroxy cyclopentane, and II) 1- (3'-4'-dihydroxy cinnamoyl) -2,5-dihydroxy cyclopentane. Other compounds isolated from the ethyl acetate extract of cherry fruits and characterized by spectral methods include: 1-(3'-methoxy, 4'-hydroxy cinnamoyl) quinic acid, 2-hydroxy-3-(2'-hydroxyphenyl) propanoic acid, methyl 2-hydroxy-3-(2'-hydroxyphenyl) propanoate, D(+)-malic acid, β-sitosterol ad β-sitosterol glucoside. FIG. 4 shows some of the phenolics which were isolated.

EXAMPLES 1 and 2

Figure 5:
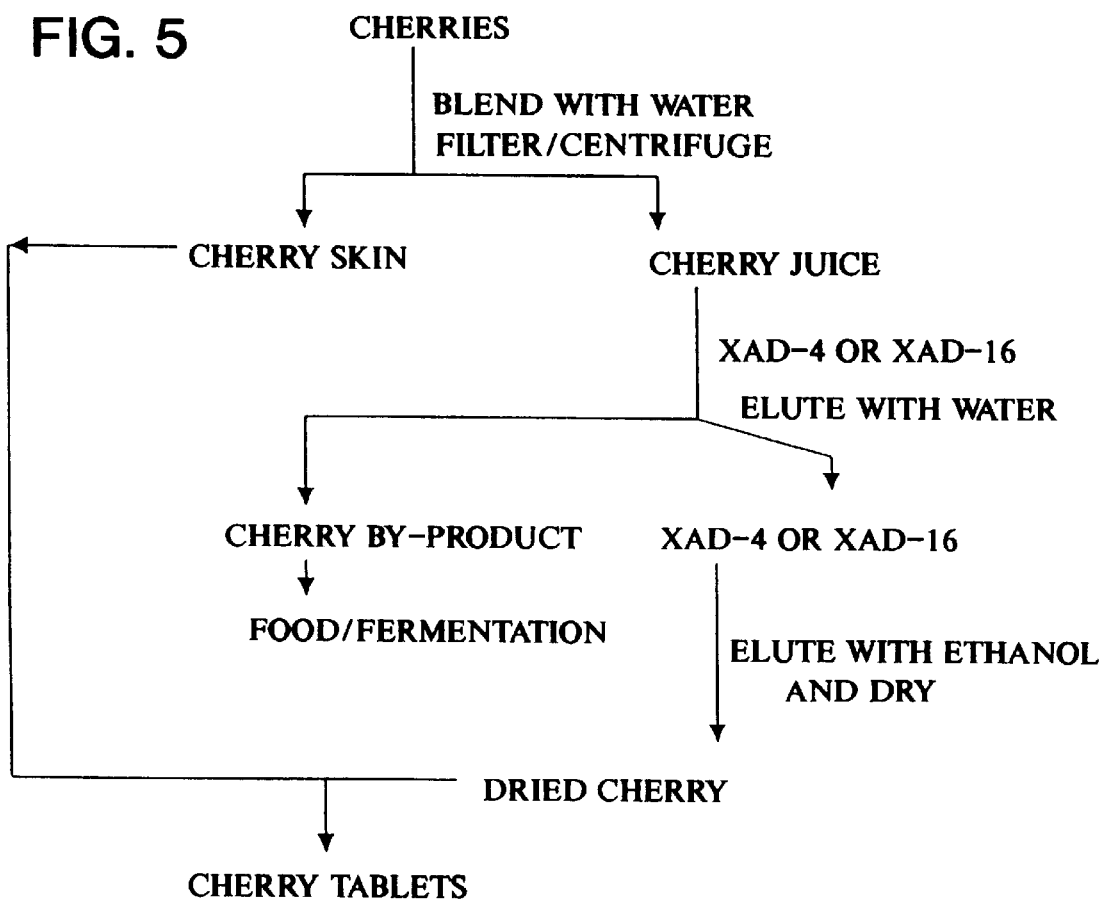
FIG. 5 shows the steps in the method of producing the preferred isolate as described in Examples 1 and 2.

As shown in FIG. 5, individual quick frozen (IQF) cherries (which had been pitted) were defrosted and blended in an industrial WARING blender. The mixture was centrifuged at 10,000 rpm and the juice was decanted. The residue, pulp, was further pressed with cheese cloth to remove any additional juice.

The pulp was lyophilized at 15° C. The juice was processed on AMBERLITE XAD-16 HP resin to produce cherry sour, anthocyanins, bioflavonoids and phenolics. The XAD-16 resin, 1 kg, was washed with ethanol (1–2 L) and then washed with water (6 L). The XAD-16 resin was allowed to stand in water for 1 hour before loading into a glass column (10 ID×90 cm long) with a cotton plug. The packed column was washed with water (2 L) before loading the juice for separation. 800 mL juice was purified each time. The juice was added onto the surface of the column and allowed to settle with no flow. It was then eluted with water and the first 1 L was discarded. The next 2 L of washing was collected, since it contained the cherry juice which was sour since it contained malic acid and sugars from the cherries. The column was then washed with an additional 4 L of water in the case of BALATON and 5 L for MONTMORENCY cherry juice. Once the cherry juice was collected, the remainder of the washing with water were discarded. The column was then eluted with ethanol (1.3–1.5 L) and collected the red solution containing anthocyanins, bioflavonoids and phenolics (700–800 ml). The column was then run dry and washed with 10 L of water before repeating the process many of times (over 100).

The red alcoholic solution was then evaporated under vacuum a (20 millitorr) to remove ethanol and the aqueous solution, stabilized with 50 ppm ascorbic acid, was lyophilized at 10° C. The red powder was collected and stored.

Example 1 results:

| BALATON cherry | |
| --- | --- |
| Weight of IQF cherries | 15.74 kg |
| Weight of dried pulp | 605 g |
| Volume of juice | 12.16 L |
| Weight of anthocyanins, bioflavonoids and phenolics (red powder) | 31.35 g |
| Volume of sour byproduct (malic acid and sugars) | @ 35 L |

Example 2 results:

| MONTMORENCY cherry | |
| --- | --- |
| Weight of IQF cherries | 30.45 kg |
| Weight of dried pulp | 895 g |
| Volume of juice | 24.03 L |
| Weight of anthocyanins, bioflavonoids and phenolics (red powder) | 47 g |
| Volume of cherry by-product (malic acid and sugars) | @ 75 L |

The red powders of Examples 1 and 2 were preferably mixed with dried pulp as a carrier and tabletted into 1 to 1000 mg tablets including the carrier (1 adult daily dose).

Various food grade acids can be added to the isolated anthocyanins, bioflavonoids and phenolics to prevent decomposition. Preferably they do not add flavor. Ascorbic acid (vitamin C) is preferred. The acid can be added before or after, preferably before drying of the cherry compounds.

For small scale processing, lyophilization is used to remove water. For larger scale production, drying in an air circulating oven is preferred.

EXAMPLE 3

Figure 6:
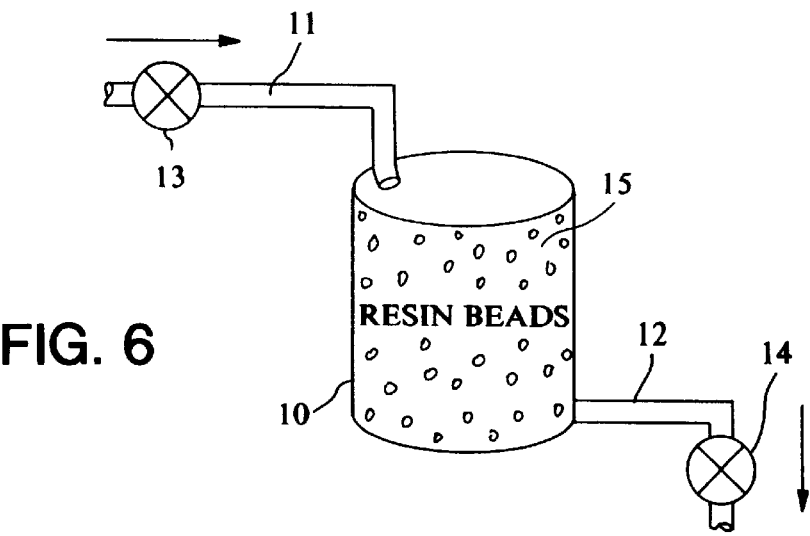
FIG. 6 is a schematic drawing showing the use of an open vessel 10 for holding resin beads, which remove anthocyanins, bioflavonoids and phenolics from the cherry juice.

As shown in FIG. 6, an open vessel 10 is provided with an inlet line 11 and an outlet line 12, with valves 13 and 14, respectively. The resin beads 15 are provided in the open vessel 10. Water is introduced into the vessel 10 and then removed through outlet line 12 and discarded. The cherry juice (without the pulp or pits) as in Example 1 is introduced to the vessel 10 and allowed to stand for 25 minutes. The temperature of the water and juice is between about 20 and 30° C. The cherry juice residue containing malic acid and sugars is then removed through the outlet line 12 and retained as a food flavoring. The resin 15 in the vessel is then washed again with water from inlet line 11 and then removed and discarded through outlet line 12. The anthocyanins, bioflavonoids and phenolics on the resin particles are then extracted using 95% ethanol introduced through inlet line 11. The ethanol containing the anthocyanins, bioflavonoids and phenolics is removed from the vessel 10. The ethanol is removed from the anthocyanins, bioflavonoids and phenolics and dried using flash drying under nitrogen. The resulting powder is preferably then mixed with dried cherry pulp or other carrier as in Example 1. The resin particles are washed with water and then the resins and ethanol are recycled many times.

EXAMPLE 4

Figure 7:
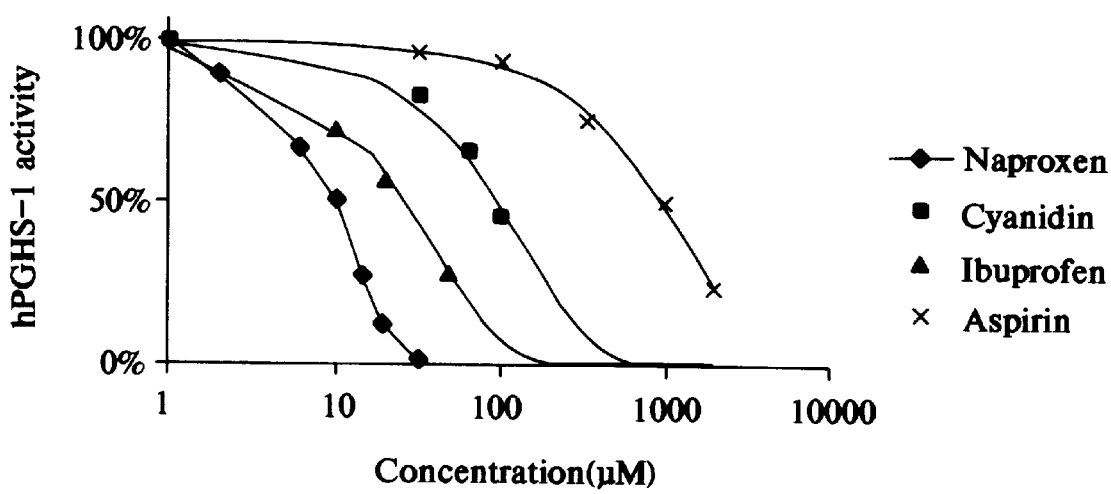
FIG. 7 is a dose-response curve for the inhibition of the human PGHS-1 enzyme by cyanidin. The antiinflammatory activity of cyanidin was estimated by its ability to inhibit the cyclooxygenase activity of the PGHS-1 enzyme. Cyanidin gave an $IC_{50}$ value of 90 $\mu$M for PGHS-1 enzyme, while the NSAID aspirin, naproxen, and ibuprofen gave $IC_{50}$ values of 1050, 11, and 25 $\mu$M, respectively.
Figure 8:
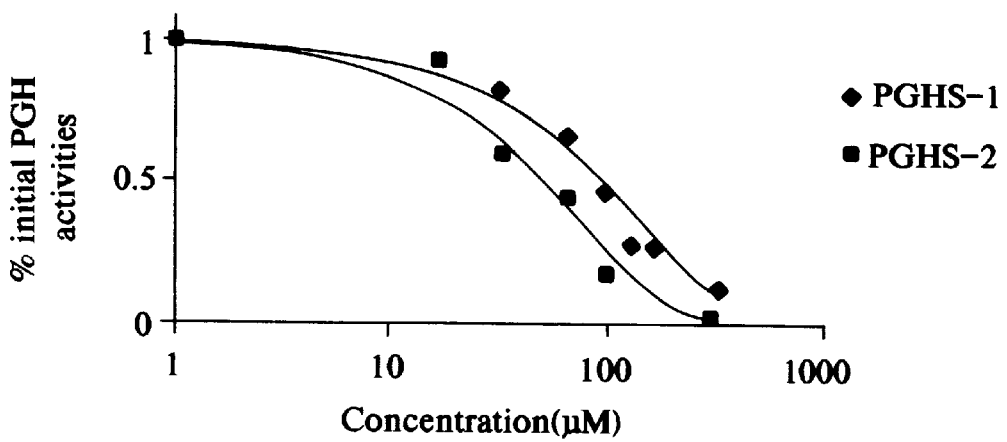
FIG. 8 is a dose-response curve for the inhibition of PGHS-1 and PGHS-2 enzymes by cyanidin. Cyanidin gave $IC_{50}$ values of 90 and 60 mM for PGHS-1 and PGHS-2 enzymes, respectively.

The antiinflammatory assays on the anthocyanins and cyanidin were conducted using prostaglandin endoperoxide H synthase-1 and -2 isozymes (PGHS-1, and -2) and were based on their ability to convert arachidonic acid to prostaglandins (PGs). The positive controls used in this experiment were aspirin, naproxen, and ibuprofen. Aspirin gave an $IC_{50}$ value of 1050 $\mu$M each against PGHS-1 and PGHS-2 enzymes (FIG. 7). Naproxen and ibuprofen gave $IC_{50}$ values of 11 and 25 nM against PGHS-1 enzyme, respectively (FIG. 7). A preliminary experiment with the mixture containing anthocyanins 1–3 (FIG. 1) showed PGHS-1 and PGHS-2 activities at 33 ppm concentration. The aglycon cyanidin showed good PGHS-1 and -2 inhibitory activities, with $IC_{50}$ values of 90 and 60 nM, respectively (FIGS. 7 and 8). The ratio of $IC_{50}$ values for PGHS-1 to PGHS-2 was about 0.56 (FIG. 8). However, pure anthocyanins 1–3 showed little or no activity against PGHS-1 and PGHS-2 at 300-nM test concentrations. Higher concentrations of anthocyanins 1 and 2, on the contrary, increased the activity of enzyme. This is probably due to the ability of anthocyanins 1 and 2 to act as oxygen carriers at high concentration and enhance the oxygen uptake. It is noted that anthocyanins are hydrolyzed in the gut of a mammal to cyanidin and other compounds and thus effective in vivo.

For measurements of time-dependent inhibition of PGHS-2 enzyme activity by cyanidin, the enzyme was preincubated at 37° C. with 15 nM of cyanidin (one-fourth of the concentration of $IC_{50}$) and added to an oxygen electrode chamber with arachidonic acid substrate to initiate the reaction. The results suggest that the rate of inhibition of PGHS-2 did not change with time.

The specific inhibition of the PGHS-2 enzyme is a major advance in antiinflammatory therapy because it significantly reduces the adverse effects of nonsteroidal antiinflammatory drugs (NSAIDs). It is generally believed that ulcerogenic and other adverse properties of NSAIDs result from the inhibition of PGHS-1, whereas the therapeutically desirable effects come from the inhibition of PGHS-2 enzyme.

Similarly, cyanidin showed better antiinflammatory activity than aspirin in the inflammatory assays. The antioxidant and antiinflammatory properties of anthocyanins and cyanidin suggest that consumption of cherries may have the potential to reduce cardiovascular or chronic diseases in humans.

In particular, arachidonic acid and a microsomal fraction of ram seminal vesicles containing PGHS-1 enzyme suspended in 100 mM Tris pH 7.8 and 300 μM diethyldithiocarbamic acid (DDC) as a preservative were purchased from Oxford Biomedical Research (Oxford, Mich.). Recombinant human PGHS-2 enzyme was initially obtained from Dr. David Dewitt (Department of Biochemistry, Michigan State University, East Lansing, Mich.) and then purchased from Oxford Biomedical Research (Oxford, Mich.). Naproxen, ibuprofen, and hemoglobin were purchased from Sigma Chemical Co. (St. Louis, Mo.). Anthocyanins 1–3 were purified from Balaton tart cherry by HPLC and were identified by $^1$H and $^{13}$C NMR spectral data.

To prepare cyanidin, the anthocyanin mixture containing 1–3 (FIG. 1; 500 mg) was stirred with 3N HCl (20 mL) at 80° C. for 10 hours. The reaction mixture was purified on a XAD-4 column as in the preparation of anthocyanins. The MeOH solution of cyanidin was evaporated to dryness to yield a red amorphous powder (190 mg) and stored at −30° C. until use.

In the antiinflammatory assay, cyclooxygenase activities were measured by using PGHS-1 enzyme (ca. 5 mg protein/mL in 0.1 M TrisHCl, pH 7.8), a homogeneous protein purified from ram seminal vesicles. Microsomal preparations from recombinant human prostaglandin synthase-2 (COX-2) were obtained from insect cell lysate. Assays were performed at 37° C. by monitoring the initial rate of $O_2$ uptake using an $O_2$ electrode (Yellow Springs Instrument Inc., Yellow Springs, Ohio). Each assay mixture contained 3 mL of 0.1 M Tris HCl, pH adjusted to 7 by the addition of 6M HCl, 1 mM phenol, 85 μg hemoglobin, and 10 μM of arachidonic acid. Reactions were initiated by the addition of 5–25 μg of microsomal protein in a volume of 15–50 μL. Instantaneous inhibition of enzyme activity was determined by measuring the cyclooxygenase activity initiated by adding aliquots of microsomal suspensions of PGHS-1 or PGHS-2 (10 μM $O_2$/min cyclooxygenase activity/aliquot) to assay mixtures containing 10 μM arachidonate and various concentrations of the test substances (10–1100 μM). The $IC_{50}$ values represent the concentrations of the test compound that gave half-maximal activity under the standard assay conditions.

EXAMPLE 5

This is an antiinflammatory assay for cyclooxygenase inhibition activity of flavonoids and isoflavonoids. Arachidonic acid and microsomal suspensions of PGHS-1 (COX-1) and COX-2 (PGHS-2) were purchased from Oxford Biomedical Research (Oxford, Mich., USA). Genistein, genistin, naringenin, quercetin, 5,8,4'-trihydroxy-6,7-dimethoxyflavone, kaempferol-3-rutinoside and 3'-methoxy kaempferol 3-rutinoside were purified from BALATON tart cherry by HPLC and were identified by $^1$H- and $^{13}$C NMR spectral data. Daidzein and formononetin were purchased from Research Plus, Inc. (Bayonne, N.J., USA). Biochanin A, kaempferol, quercetin, naproxen, ibuprofen and hemoglobin were purchased from Sigma Chemical Co. (St. Louis, Mo., USA). Luteolin was purchased from Adams Chemical Co. (Round Lake, Ill., USA).

For measuring the COX activity, flavonoids or isoflavonoids were dissolved in DMSO to yield 40 mM stock solution and was further diluted to the desired concentration according to the COX-1/COX-2 inhibitory activity of each compound assayed.

Anti-inflammatory assay: COX activities were measured using microsomal suspensions of PGHS-1 and PGHS-2. Microsomal membranes (5 mg protein/mL in 0.1 M Tris HCl, pH 7.4) were prepared and assayed on the same day. COX-1 and COX-2 assay was performed at 37° C. controlled by a circulation bath (Model-1166, VWR Scientific Products, Chicago, Ill.) by monitoring the rate of $O_2$ uptake using a 5357 Oxygen electrode (INSTECH Laboratory, Plymouth Meeting, Pa.) (Meade, E. A., et al., J. Biol. Chem. 268 6610–6614 (1993)).

Each assay mixture contained 600 μL of 0.1 M Tris-HCl, pH 8.0, 1 mM phenol, 17 μg hemoglobin and 10 μM arachidonate and were mixed in a microchamber (INSTECH Laboratory, Plymouth Meeting, Pa., USA). For anthocyanins and cyanidin pH 7 is preferred to prevent decomposition in absence of additives. Reactions were initiated by adding 5 μg of microsomal protein (5 μL). Instantaneous inhibition was determined by measuring the cyclooxygenase activity initiated by adding microsomal suspensions of PGHS-1 or PGHS-2 in the assay mixtures containing 10 μM arachidonate and various concentrations of test compounds. The $IC_{50}$ values represent the concentrations of inhibitor that gave half-maximal activity under the standard assay conditions. The kinetics of the enzyme activity was monitored by Biological Oxygen Monitor (YSI model 5300, Yellow Springs Instrument CO., Inc., Yellow Springs, Ohio) and collected in Quicklog Data Acquisition and Control computer software (Strawberry Tree Inc., Sunnyvale, Calif., USA).

The COX-1/COX-2 activity of BALATON cherry bioflavonoids was determined by monitoring the $O_2$ uptake. Reactions were initiated by adding PGHS enzyme preparation. One unit of cyclooxygenase represents oxygenation of 1 nmol of arachidonate/min under the standard assay condition by the COX enzyme. This assay was a modification of the assay reported by DeWitt et al. (Dewitt D. L., et al., J. Biol. Chem. 265 5192–5198 (1990)). 10 μM arachidonate has been used for COX-1 assays, because this substrate concentration was reported to give near-maximal COX activity and also permit the detection of enzyme inhibition by lipophilic inhibitors (Meade, E. A., et al., Biol. Chem. 268 6610–6614 (1993)). This methodology can also be used for COX-2 assay as well using COX-2 enzyme. Three known COX inhibitors, aspirin, ibuprofen and naproxen, were selected as positive controls. COX-1 inhibitory activities of flavonoids, kaempferol, quercetin, luteolin, quercetin 3-rhamnoside, 5,8,4'-trihydroxy-6,7-dimethoxyflavone were compared. Kaempferol 3-rutinoside, 3'-methoxy kaempferol 3-rutinoside and naringenin (FIG. 9), and five isoflavonoids, genistein, genistin, daidzein, formononetin and biochanin A (FIG. 8).

Figure 10:
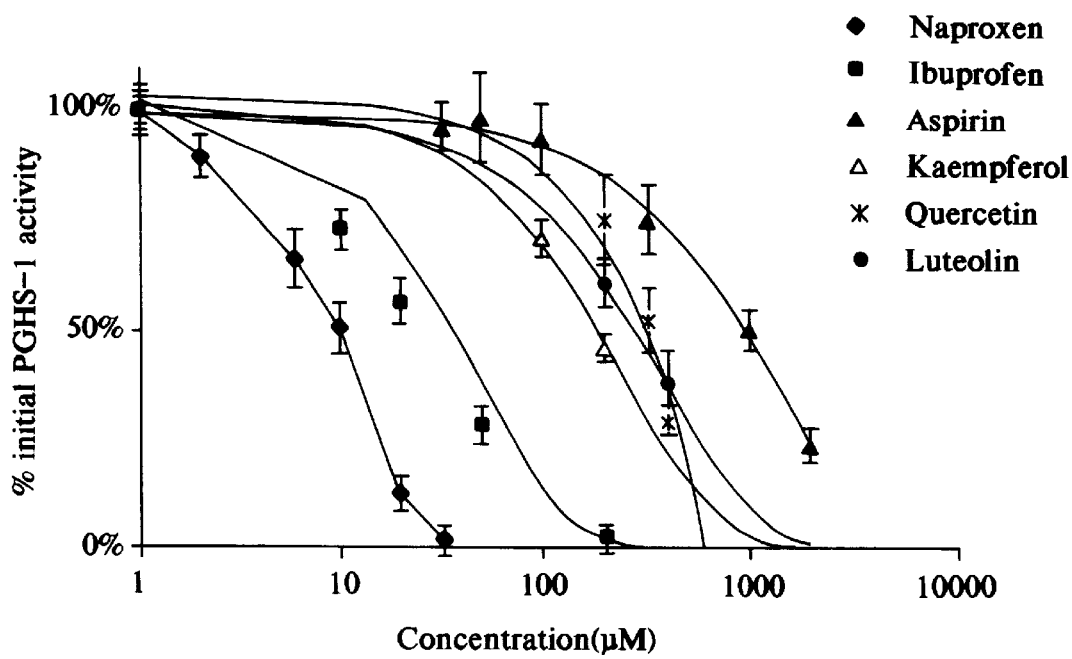
FIG. 10 is a graph showing dose response curves for the inhibition of the PGHS-1 enzyme (COX-1) by flavonoids from BALATON tart cherries compared to the non-steroidal anti-inflammatory drugs, naproxen, aspirin, and ibuprofen. The $IC_{50}$ of kaempferol, quercetin, luteolin, aspirin, naproxen and ibuprofen are 180, 350, 300, 1050, 11 and 25 $\mu$M, respectively. Data is expressed as mean ±S.E. of triplicate.
Figure 11:
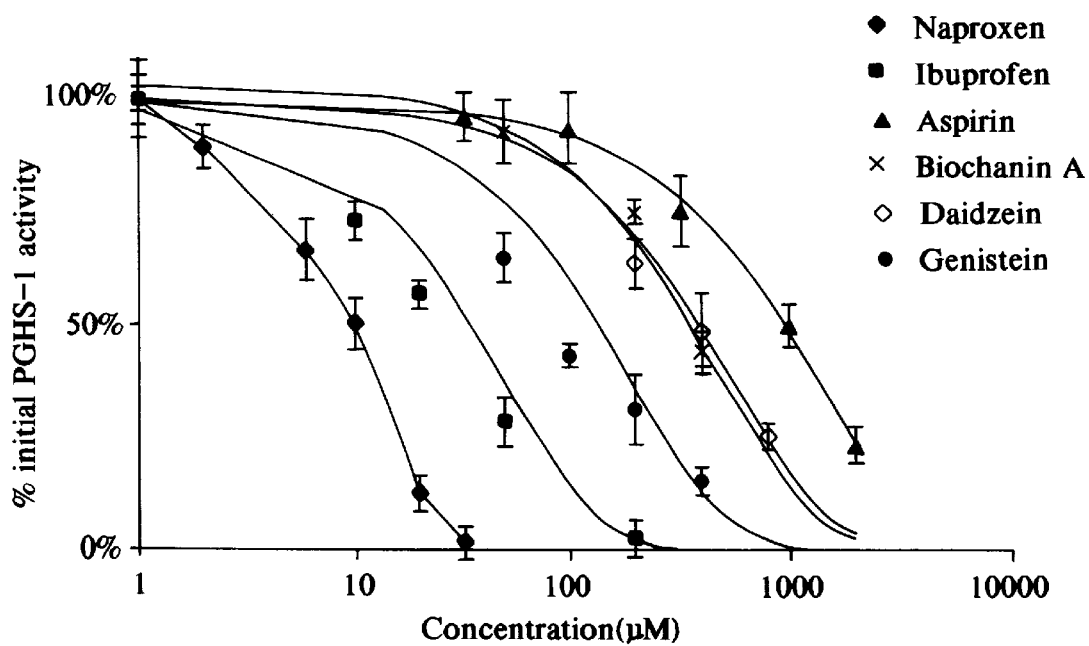
FIG. 11 are graphs showing dose response curve for the inhibition of the PGHS-1 enzyme (COX-1) by isoflavonoids from BALATON tart cherries compared to the non-steroidal anti-inflammatory drugs, naproxen, aspirin and ibuprofen. The $IC_{50}$ of daidzein, biochanin A, genistein, aspirin, naproxen and ibuprofen are 400, 350, 80, 1050, 11 and 25 $\mu$M, respectively. Data is expressed as mean ±S.E. of triplicate.

COX-1/COX-2 inhibitory activities of each compound at different concentrations was calculated by comparing the tangent of $O_2$ uptake curves of test compounds with that of blank control. Each assay was repeated 3 times and the $IC_{50}$ values (50 inhibitory concentrations) were calculated by linear regression analysis. The half-maximal inhibitory concentrations of flavonoids and isoflavonoids are shown in FIG. 11. Dose response curves for the inhibition of the COX-1 enzyme by flavonoids and isoflavonoids from BALATON tart cherries compared to the non-steroidal anti-inflammatory drugs, aspirin, naproxen and ibuprofen are shown in FIGS. 10 and 11, respectively.

Figure 9:
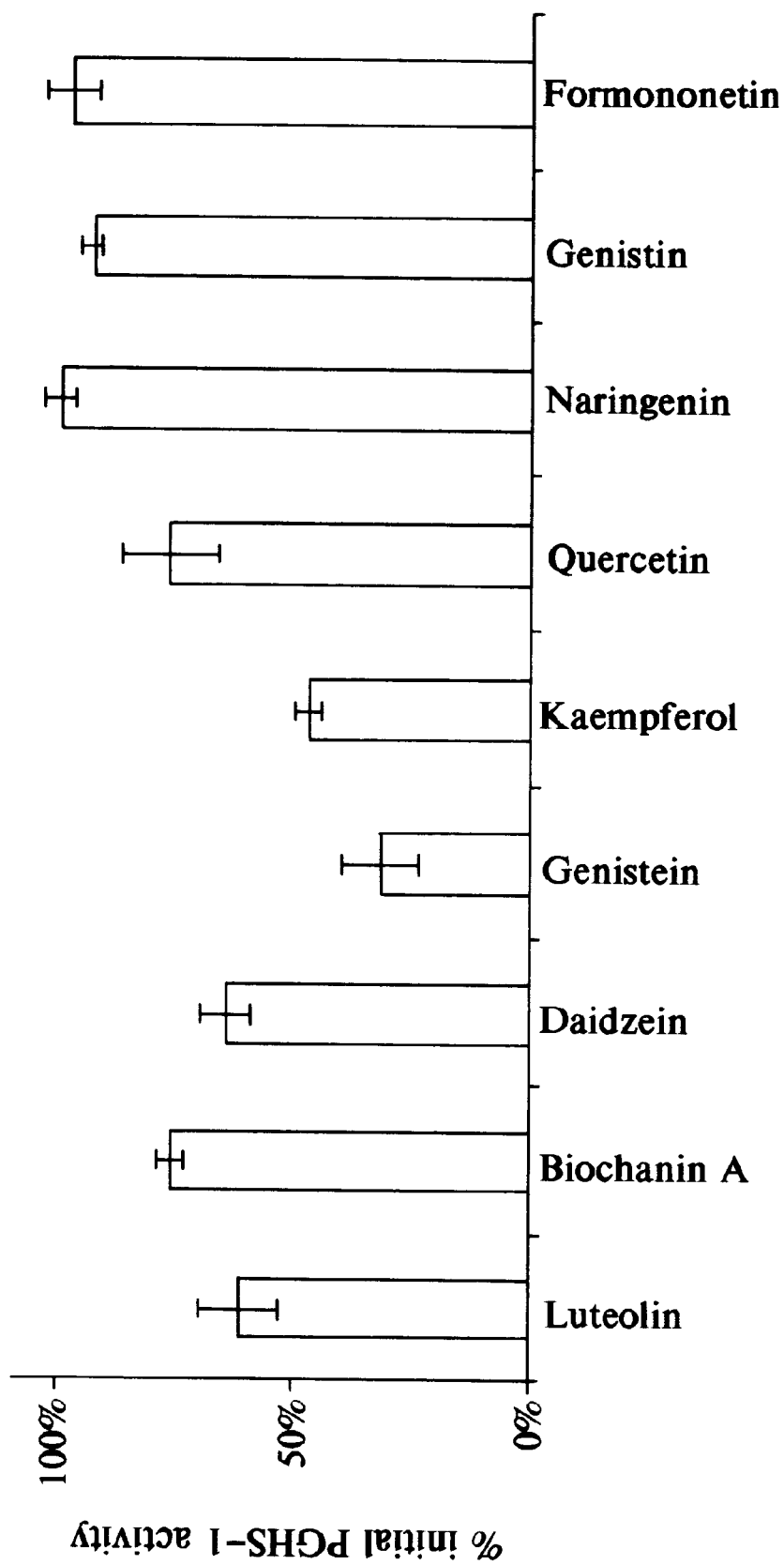
FIG. 9 is a graph showing the inhibitory effect of PGHS-1 (COX-1) by flavonoids and isoflavonoids at 200 $\mu$m concentrations. Data is expressed as mean ±S.E. of triplicate. Kaempferol 3-rutinoside, 3'-methoxy kaempferol 3-rutinoside, 5,8,4'-trihydroxy-6,7-dimethoxyflavone and quercetin were not active at 1000 $\mu$M concentrations.

Among the flavonoids tested, kaempferol showed the highest COX-1 inhibition, followed by luteolin, quercetin, naringenin and quercetin 3-rhamnoside (FIG. 9). In comparing kaempferol with quercetin, it was found that the presence of a hydroxyl group at $C_3$' position decreased the COX-1 inhibitory activity (FIG. 9). The COX-1 inhibitory activity of kaempferol and quercetin were reported in other model systems (Kalkbrenner, F., et al., Pharmacology 44 1–12 (1992); Hoult, J. R. S., et al., Agents and Actions 42 787–792 (1988); and Moroney, M. A., et al., J. Pharm. Pharmacol. 40 787–792 (1988)). The OH group at $C_3$ position is also important for the activity. However, the glycosylation of the OH group at $C_3$ decreased the activity considerably. Comparing the COX-1 inhibitory activity of flavones (luteolin) with their corresponding flavanols (quercetin), it can be concluded that the absence of an OH group at $C_3$ enhanced the COX-1 activity slightly. It is important to note that quercetin 3-rhamnoside was not active in the assay, but reported to have in vivo anti-inflammatory activity (Sanchez De Medina, L. H., et al., J. Pharmacol. Exp. Ther. 278 771–779 (1996)). This may be due to the in vivo metabolism of quercetin 3-rhamnoside to quercetin. The $C_2$–$C_3$ double bond, which determines the coplanarity of the hetero-rings in flavonoids and isoflavonoids, was essential for a higher COX inhibitory activity. If the double bond was saturated, the COX-1 inhibitory effect was dramatically decreased as in the case of naringenin (FIG. 9). This result is consistent with previous reports (Wurm, G., et al., Deutche Apotheker Zeitung 122 2062–2068 (1982); Kalkbrenner, F., et al., Pharmacology 44 1–12 (1992)). Also, the multiple substituents such as OH and OMe groups in the A ring of the flavonoids caused little or no COX-1 inhibition as demonstrated by the activity of 5,8,4-–trihydroxy-6,7-dimethoxyflavone.

Among the isoflavonoids (FIGS. 2 and 3), genistein showed the highest COX-1/COX-2 inhibitory activity. The activity was dramatically decreased in genistin, when the 7-OH group in ring A of genistein was glycosylated. Also, the hydroxyl group at C-4' in isoflavonoids is essential for the COX-1/COX-2 inhibitory activity. When 4'-OH groups in genistein and daidzein were methylated, the activity decreased considerably. The 5-OH group in isoflavonoids is also important for COX-1/COX-2 inhibitory effect. These results indicated that $C_4'$, $C_5$ and $C_7$ hydroxyl groups in isoflavonoids are essential for COX-1 inhibition. Comparison of genistein with that of kaempferol indicates that substitutions on ring B and at $C_3$ of ring C enhances COX-1/COX-2 inhibitory effect. In addition to COX-1/COX-2 inhibition, these isoflavonoids and flavonoids also showed good antioxidant activity. Both COX-1 inhibitory and antioxidant activities of these compounds suggests that tart cherries may possess significant health benefits to humans. These bioflavonoids may be partially responsible for the anecdotal claims associated with tart cherries of alleviating pain related to treatment of arthritis and gout.

Thus several flavonoids and isoflavonoids isolated from BALATON tart cherry were assayed for prostaglandin H endoperoxide synthase (PGHS-1 or PGHS-2) enzyme activity. Genistein showed the highest COX-1 inhibitory activity among the isoflavonoids studied with an $IC_{50}$ value of 80 µM. Kaempferol gave the highest COX-1 inhibitory activity among the flavonoids tested with an $IC_{50}$ value of 180 µM. The structure-activity relationships of flavonoids and isoflavonoids revealed that hydroxyl groups at $C_4'$, $C_5$ and $C_7$ in isoflavonoids were essential for appreciable COX-1 inhibitory activity. Also, the $C_2$–$C_3$ double bond in flavonoids is important for COX-1 inhibitory activity. However, hydroxyl group at $C_3'$ position decreased the COX-1/COX-2 inhibitory activity by flavonoids.

EXAMPLE 6

The composition of Examples 1 and 2 were tested for anti-inflammatory activity using cyclooxygenase 1 and 2 (COX-1 and COX-2) in an assay as described in Wang et al., J. Nat. Products 62:294–296 (1999); Wang et al., J. of Ag. and Food Chemistry, 47: 840–844 (1999) and Wang et al., J. of Nat. Products, 62:86–88 (1999) and Examples 4 and 5. The results were that the compositions exhibited anti-inflammatory activities, specifically strong inhibition of COX-1 and COX-2.

It is intended that the foregoing description be only illustrative of the present invention and that the present invention be limited only by the hereinafter appended claims.

We claim:

1. A method for inhibiting cyclooxygenase or prostaglandin H synthase enzymes comprising:
   providing at least one compound anthocyanin selected from the group consisting of cyanidin-3-glucosylrutinoside, cyanidin-3-rutinoside and or cyanidin-3-glucoside isolated from the fruit of a cherry to inhibit the enzymes.

2. The method of claim 1 wherein the method is in vitro.

3. The method of claim 1 wherein the method is in vivo.

4. The method of any one of claims 1, 2 or 3 wherein the compound is from a tart cherry.

5. The method of any one of claims 1, 2 or 3 wherein the compound is isolated from a sweet cherry.

6. A method for inhibiting inflammation in a mammal comprising:
   administering to a mammal in need of such treatment, an effective amount of at least one anthocyanin obtained from the fruit of a cherry, said anthocyanin selected from the group consisting of cyanidin-3-glucosylrutinoside, cyanidin-3-rutinoside, and cyanidin-3-glucoside and mixtures thereof to inhibit said inflammation.

7. The method of claim 6 wherein said anthocyanin is obtained from *Prunus avium, Prunus cerasus,* and mixtures thereof.

8. The method of claim 6 wherein said anthocyanin is obtained from *Prunus cerasus.*

* * * * *

UNITED STATES PATENT AND TRADEMARK OFFICE
CERTIFICATE OF CORRECTION

PATENT NO. : 6,194,469 B1
DATED : February 27, 2001
INVENTOR(S) : Muraleedharan G. Nair, Haibo Wang, Gale M. Strasburg, Alden M. Booren and James I. Gray It is certified that error appears in the above-identified patent and that said Letters Patent is hereby corrected as shown below:

Column 3,
Line 48, "incudes" should be -- includes --.

Column 7,
Line 23, "many of times" should be -- many times --.

Column 9,
Line 12, "Balaton" should be -- BALATON --.

Column 11,
Line 27, "5, 8, 4-trihydroxy" should be -- 5, 8, 4' - trihydroxy --.

Column 12,
Line 28, (Claim 1), "compound" after "one" and before "anthocyanin" should be deleted.

Signed and Sealed this

Sixteenth Day of October, 2001

Attest:

NICHOLAS P. GODICI
Attesting Officer
Acting Director of the United States Patent and Trademark Office